(12) United States Patent  (10) Patent No.: US 8,714,741 B2
Donoso et al. (45) Date of Patent: May 6, 2014

(54) METHOD FOR SELECTING IMAGES

(75) Inventors: Larry Donoso, Philadelphia, PA (US); Michael DellaVecchia, Berwyn, PA (US)

(73) Assignee: Philadelphia Retina Endowment Fund, Philadelphia, PA (US)

( * ) Notice: Subject to any disclaimer, the term of this patent is extended or adjusted under 35 U.S.C. 154(b) by 932 days.

(21) Appl. No.: 12/856,669

(22) Filed: Aug. 15, 2010

(65) Prior Publication Data

US 2010/0303308 A1 Dec. 2, 2010

Related U.S. Application Data

(63) Continuation of application No. 12/121,038, filed on May 15, 2008, now Pat. No. 7,775,665, which is a continuation-in-part of application No. 10/696,046, filed on Oct. 29, 2003, now Pat. No. 7,377,647, which is a continuation-in-part of application No. 10/011,187, filed on Nov. 13, 2001, now Pat. No. 6,648,473.

(51) Int. Cl.
A61B 3/10 (2006.01)
A61B 3/14 (2006.01)
A61B 3/103 (2006.01)

(52) U.S. Cl.
CPC ..................... A61B 3/103 (2013.01)
USPC ............ 351/205; 351/206; 351/210; 351/221

(58) Field of Classification Search
USPC .......... 351/205, 206, 210, 212, 246, 247, 221
See application file for complete search history.

(56) References Cited

U.S. PATENT DOCUMENTS

| | | |
|---|---|---|
| 4,619,508 A | 10/1986 | Shibuya |
| 4,641,349 A | 2/1987 | Flom |
| 5,029,220 A | 7/1991 | Juday |
| 5,291,560 A | 3/1994 | Daugman |
| 5,359,669 A | 10/1994 | Shanley |
| 5,719,950 A | 2/1998 | Osten |
| 5,751,836 A | 5/1998 | Wildes |
| 5,777,719 A | 7/1998 | Williams |
| 5,912,731 A | 6/1999 | DeLong |
| 5,949,521 A | 9/1999 | Williams |
| 6,007,204 A | 12/1999 | Fahrenkrug |
| 6,019,472 A | 2/2000 | Koester |
| 6,086,204 A | 7/2000 | Magnante |
| 6,095,651 A | 8/2000 | Williams |
| 6,143,011 A | 11/2000 | Hood |
| 6,155,684 A | 12/2000 | Billie |
| 6,289,113 B1 | 9/2001 | McHugh |
| 6,305,803 B2 | 10/2001 | Sumiya |
| 6,377,699 B1 | 4/2002 | Musgrave |
| 6,526,160 B1 | 2/2003 | Haruo |
| 6,532,298 B1 | 3/2003 | Cambier |
| 6,539,100 B1 | 3/2003 | Amir |
| 6,542,624 B1 | 4/2003 | Oda |
| 6,546,121 B1 | 4/2003 | Oda |
| 6,549,118 B1 | 4/2003 | Seal |

(Continued)

OTHER PUBLICATIONS

Liang et al., "Supernormal . . . optics," J Op Soc Amer A, 14(11)2884-2891, 1997.

(Continued)

Primary Examiner — Jack Dinh
(74) Attorney, Agent, or Firm — MDIP LLC

(57) ABSTRACT

A method for selecting an image is presented.

6 Claims, 8 Drawing Sheets

(56) References Cited

U.S. PATENT DOCUMENTS

| | | |
|---|---|---|
| 6,556,699 B2 | 4/2003 | Rogers |
| 6,575,574 B2 | 6/2003 | Della Vecchia |
| 6,594,377 B1 | 7/2003 | Kim |
| 6,614,919 B1 | 9/2003 | Suzaki |
| 6,648,473 B2 | 11/2003 | DellaVecchia |
| 6,961,448 B2 | 11/2005 | Nichols |
| 7,226,166 B2 | 6/2007 | Della Vecchia |
| 7,377,647 B2 | 5/2008 | Della Vecchia |
| 7,561,183 B1 | 7/2009 | Schaffner |
| 7,775,665 B2 | 8/2010 | DellaVecchia |
| 2001/0026632 A1 | 10/2001 | Tamai |
| 2002/0057438 A1 | 5/2002 | Decker |
| 2002/0080256 A1 | 6/2002 | Bates et al. |
| 2002/0084904 A1 | 7/2002 | De la Huerga |
| 2002/0132663 A1 | 9/2002 | Cumbers |
| 2002/0158750 A1 | 10/2002 | Amalik |
| 2003/0018522 A1 | 1/2003 | Denimarck et al. |
| 2003/0095689 A1 | 5/2003 | Volkommer |
| 2003/0120934 A1 | 6/2003 | Ortiz |
| 2009/0074257 A1 | 3/2009 | Della Vecchia |

OTHER PUBLICATIONS

Vargas et al., "Correction . . . performance," J Op Soc Amer A 15(9)2552, 1998.

Liang et al., "Objective . . . sensor," J Op Soc Amer A 11(7)1949, 1994.

Vorontsov et al., "Stochastic . . . correction," J Op Soc Amer A 15(10)2745, 1998.

Vorontsov et al., "Adaptive . . . optimization," Op Lett 22(12)907, 1997.

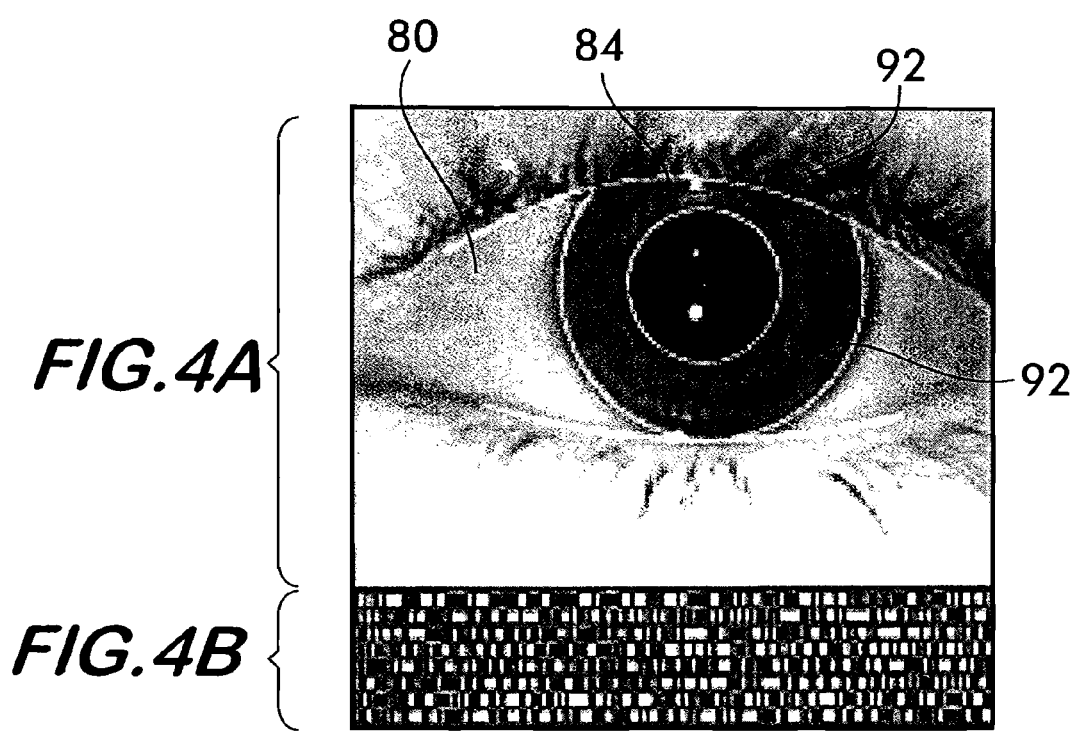

METHOD FOR SELECTING IMAGES

BACKGROUND OF THE INVENTION

1. Field of Invention

This invention relates to a method and a system for high-resolution retinal imaging, eye aberration compensation, and diagnostics based on adaptive optics with direct optimization of an image quality metric using a stochastic parallel perturbative gradient descent technique.

Adaptive optics is a promising technique for both diagnostics of optical aberrations of the eye and substantially aberration-free high-resolution imaging of the retina. In existing adaptive optics techniques adaptive correction is based on illumination of the retina by a collimated laser beam to create a small size laser location on the retina surface with consequent measurement of phase aberrations of the wave scattered by the retina tissue. Correction of eye optical aberrations is then performed using the conventional phase conjugation technique.

This traditional approach has several important drawbacks. One important drawback is the danger due to an invasive use of the laser beam focused onto the retina. Other drawbacks include overall system complexity and the high cost of the necessary adaptive optics elements such as a wavefront sensor and wavefront reconstruction hardware. More importantly, due to aberrations the laser beam location size on the retina is not small enough to use it as a reference point-type light source and hence conjugation of the measured wavefront does not result in optimal optical aberration correction. Additionally, the traditional approach can produce a turbid image that can make performing an operation with a microscope difficult.

One prior art method using a laser is taught in U.S. Pat. No. 6,095,651 entitled "Method and Apparatus for Improving Vision and the Resolution of Retinal Images", issued to Williams, et al. on Aug. 1, 2000. In Williams, et al. teaches a method and apparatus for improving resolution of retinal images. In this method, a point source of light is produced on the retina by a laser beam. The source is reflected from the retina and received at a lenslet array of a Hartman-Shack wavefront sensor. Thus, higher order aberrations of the eye can be measured and data can be obtained for compensating the aberrations using a system including a laser. U.S. Pat. Nos. 5,777,719 and 5,949,521 provide essentially the same teachings. While these references teach satisfactory methods for compensating aberrations, there is some small risk of damaging the retina since these methods require applying laser beams to the retina.

U.S. Pat. No. 5,912,731, entitled "Hartmann-type Optical Wavefront Sensor" issued to DeLong, et al. on Jun. 5, 1999 teaches an adaptive optics system using adjustable optical elements to compensate for aberrations in an optical beam. The aberrations may be caused, for example, by propagation of the beam through the atmosphere. The aberrated beam can be reflected from a deformable mirror having many small elements, each having an associated separate actuator.

Part of the reflected beam taught by DeLong can be split off and directed to impinge on a sensor array which provides measurements indicative of the wavefront distortion in the reflected beam. The wavefront distortion measurements can then be fed back to the deformable mirror to provide continuous corrections by appropriately moving the mirror elements. Configurations such as this, wherein the array of small lenses as referred to as a lenslet array, can be referred to as Shack-Hartmann wavefront sensors.

Additionally, DeLong teaches a wavefront sensor for use in measuring local phase tilt in two dimensions over an optical beam cross section, using only one lenslet arrangement and one camera sensor array. The measurements of DeLong are made with respect to first and second orthogonal sets of grid lines intersecting at points of interest corresponding to positions of optical device actuators. While this method does teach the way to correct aberrations in a non-laser light system, it cannot be used in cases where lasers are required.

U.S. Pat. No. 6,007,204 issued to Fahrenkrug, et al. entitled "Compact Ocular Measuring System", issued on Dec. 28, 1999, teaches a method for determining refractive aberrations of the eye. In the system taught by Fahrenkrug, et al. a beam of light is focused at the back of the eye of the patient so that a return light path from the eye impinges upon a sensor having a light detecting surface. A micro optics array is disposed between the sensor and the eye along the light path. The lenslets of the micro optics array focus incremental portions of the outgoing wavefront onto the light detecting surface so that the deviations and the positions of the focused portions can be measured. A pair of conjugate lenses having differing focal lengths is also disposed along the light path between the eye and the micro optics array.

U.S. Pat. No. 6,019,472, issued to Koester, et al. entitled "Contact Lens Element For Examination or Treatment of Ocular Tissues" issued on Feb. 1, 2000 teaches a multi-layered contact lens element including a plurality of lens elements wherein a first lens element has a recess capable of holding a volume of liquid against a cornea of the eye. A microscope is connected to the contact lens element to assist in the examination or treatment of ocular tissues.

U.S. Pat. No. 6,086,204, issued to Magnante entitled "Methods and Devices To Design and Fabricate Surfaces on Contact Lenses and On Corneal Tissue That Correct the Eyes Optical Aberrations" on Jul. 11, 2000. Magnante teaches a method for measuring the optical aberrations of an eye either with or without a contact lens in place on the cornea. A mathematical analysis is performed on the optical aberrations of the eye to design a modified shape for the original contact lens or cornea that will correct the optical aberrations. An aberration correcting surface is fabricated on the contact lense by a process that includes laser ablation and thermal molding. The source of light can be coherent or incoherent.

U.S. Pat. No. 6,143,011, issued to Hood, et al. entitled "Hydrokeratome For Refractive Surgery" issued on Nov. 7, 2000 teaches a high speed liquid jet for forming an ophthalmic incisions. The Hood, et al. system is adapted for high precision positioning of the jet carrier. An airway beam may be provided by a collimated LED or laser diode. The laser beam can be used to align the system.

U.S. Pat. No. 6,155,684, issued to Billie, et al. entitled "Method and Apparatus for Pre-compensating The Refractive Properties of the Human Eye With Adaptive Optical Feedback Control" issued on Dec. 5, 2000. Billie, et al. teaches a system for directing a beam of light through the eye and reflecting the light from the retina. A lenslet array is used to obtain a digitized acuity map from the reflected light for generating a signal that programs an active mirror. In accordance with the signal the optical paths of individuals beams in and the beam of light are made to appear to be substantially equal to each other. Thus, the incoming beam can be precompensated to allow for the refractive aberrations of the eyes that are evidenced by the acuity map.

Additional methods for using adaptive optics to compensate for aberrations of the human eye are taught in J. Liang, D. Williams and D. Miller, "Supernormal Vision and High-Resolution Retinal Imaging Through Adaptive Optics," J.

Opt. Soc. Am. A, Vol. 14, No. 11, pp. 2884-2891, 1997 and F. Vargas-Martín, P. Prieto, and P. Artal, "Correction of the Aberrations in the Human Eye with a Liquid-Crystal Spatial Light Modulator: Limits to Performance," J. Opt. Soc. Am. A, Vol. 15, No. 9, pp. 2552-2561, 1998. Additionally, J. Liang, B. Grimm, S. Goelz, and J. Bille, "Objective Measurement of Wave Aberrations of the Human Eye with the Use of a Hartmann-Shack Wave-Front Sensor," J. Opt. Soc. Am. A, Vol. 11, No. 7, pp. 1949-1957, 1994 teaches such a use of adaptive optics.

Furthermore, it is known in the art to use a PSPGD optimization algorithm in different applications. For example, see M. Vorontsov, and V. Sivokon, "Stochastic Parallel-Gradient-Descent Technique for High-Resolution Wave-Front Phase-Distortion Correction," J. Opt. Soc. Am. A, Vol. 15, No. 10, pp. 2745-2758, 1998. Also see M. Vorontsov, G. Carhart, and J. Ricklin, "Adaptive Phase-Distortion Correction Based on Parallel Gradient-Descent Optimization," Optics Letters, Vol. 22, No. 12, pp. 907-909, 1997.

It is well known in the art to scan an iris and obtain an iris biometric image. See, for example, U.S. Pat. Nos. 4,641,349, 5,291,560, 5,359,669, 5,719,950, 6,289,113, 6,377,699, 6,526,160, 6,532,298, 6,539,100, 6,542,624, 6,546,121, 6,549,118, 6,556,699, 6,594,377, 6,614,919, and U.S. Patent Application Nos. 20010026632A1, 20020080256A1, 20030095689A1, 20030120934A1, 20020057438A1, 20020132663A1, 20030018522A1, 20020158750A1. However, such images were often not optimal and their applicability was somewhat limited.

2. Description of Related Art

All references cited herein are incorporated herein by reference in their entireties.

BRIEF SUMMARY OF THE INVENTION

The invention includes a method for clarifying an optical/digital image of an object to perform a procedure on an object having the steps of applying to the object a light beam formed of incoherent light and reflecting the applied incoherent light beam from the object to provide a reflected light beam and providing electrical signals representative of the reflected light beam. An image quality metric is determined in accordance with the electrical signals and an image is determined in accordance with the image quality metric. The procedure is performed in accordance with the image quality metric.

In a further method of the invention a procedure is performed on an eye having an iris. An iris biometric image representative of the iris is obtained and the procedure is performed on an eye in accordance with the iris biometric image.

Additionally a method for optimizing electromagnetic energy in a system for processing an image of an object in order to perform a procedure on an object is provided. The method includes applying to the object a plurality of light beams formed of incoherent light at a plurality of differing frequencies and reflecting the plurality of applied incoherent light beams from the object to provide a plurality of reflected light beams. The method also includes providing a corresponding plurality of electrical signals representative of the reflected light beams of the plurality of reflected light beams and determining a corresponding plurality of image quality metrics in accordance with the plurality of electrical signals. A corresponding plurality of images is determined in accordance with the plurality of image quality metrics and an image of the plurality of images is selected in accordance with a predetermined image criterion to provide a selected image. The method also includes determining a frequency of the plurality of differing frequencies in accordance with the selected image to provide a determined frequency and performing the procedure on an object in accordance with the determined frequency.

The inventions also deals with new methods of high-resolution imaging and construction of images of the retina, and adaptive correction and diagnostics of eye optical aberrations, as well as such imaging of articles of manufacture, identifying articles and controlling a manufacturing process. Additionally, the method is applicable to identifying individuals in accordance with such images for medical purposes and for security purposes, such as a verification of an identity of an individual. These applications can be performed using adaptive optics techniques based on parallel stochastic perturbative gradient descent (PSPGD) optimization. This method of optimization is also known as simultaneous perturbation stochastic approximation (SPSA) optimization. Compensation of optical aberrations of the eye and improvement of retina image resolution can be accomplished using an electronically controlled phase spatial light modulator (SLM) as a wavefront aberration correction interfaced with an imaging sensor and a feedback controller that implements the PSPGD control algorithm.

Examples of the electronically-controlled phase SLMs include a pixelized liquid-crystal device, micro mechanical mirror array, and deformable, piston or tip-tilt mirrors. Wavefront sensing can be performed at the SLM and the wavefront aberration compensation is performed using retina image data obtained with an imaging camera (CCD, CMOS etc.) or with a specially designed very large scale integration imaging chip (VLSI imager). The retina imaging data are processed to obtain a signal characterizing the quality of the retinal image (image quality metric) used to control the wavefront correction and compensate the eye aberrations.

The image quality computation can be performed externally using an imaging sensor connected with a computer or internally directly on an imaging chip. The image quality metric signal is used as an input signal for the feedback controller. The controller computes control voltages applied to the wavefront aberration correction. The controller can be implemented as a computer module, a field programmable gate array (FPGA) or a VLSI micro-electronic system performing computations required for optimization of image quality metrics based on the PSPGD algorithm.

The use of the PSPGD optimization technique for adaptive compensation of eye aberration provides considerable performance improvement if compared with the existing techniques for retina imaging and eye aberration compensation and diagnostics, and therapeutic applications. The first advantage is that the PSPGD algorithm does not require the use of laser illumination of the retina and consequently significantly reduces the risk of retina damage caused by a focused coherent laser beam. A further advantage is that the PSPGD algorithm does not require the use of a wavefront sensor or wavefront aberration reconstruction computation. This makes the entire system low-cost and compact if compared with the existing adaptive optics systems for retina imaging. Additionally, the PSPGD algorithm can be implemented using a parallel analog, mix-mode analog-digital or parallel digital controller because of its parallel nature. This significantly speeds up the operations of the PSPGD algorithm, providing continuous retina image improvement, eye aberration compensation and diagnostics.

Thus, in the adaptive correction technique of the present invention neither laser illumination nor wavefront sensing are required. Optical aberration correction is based on direct optimization of the quality of an retina image obtained using a white light, incoherent, partially coherent imaging system. The novel imaging system includes a multi-electrode phase spatial light modulator, or an adaptive mirror controlled with a computer or with a specially designed FPGA or VLSI system. The calculated image quality metric is optimized using a parallel stochastic gradient descent algorithm. The adaptive optical system is used in order to compensate severe optical aberrations of the eye and thus provide a high-resolution image and/or of the retina tissue and the eye aberration diagnostic.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

Figure 1A:
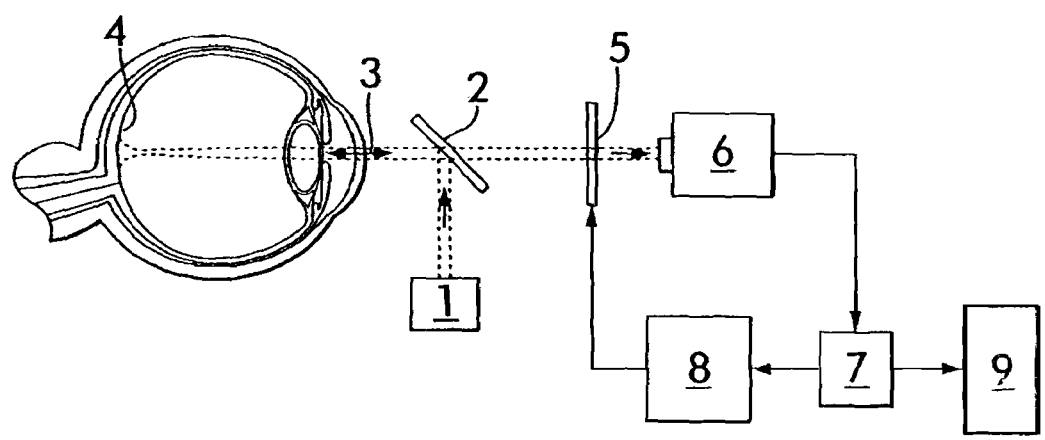
FIGS. 1A,B show a schematic representation of system suitable for practicing the eye aberration correcting method of the present invention.
Figure 1B:
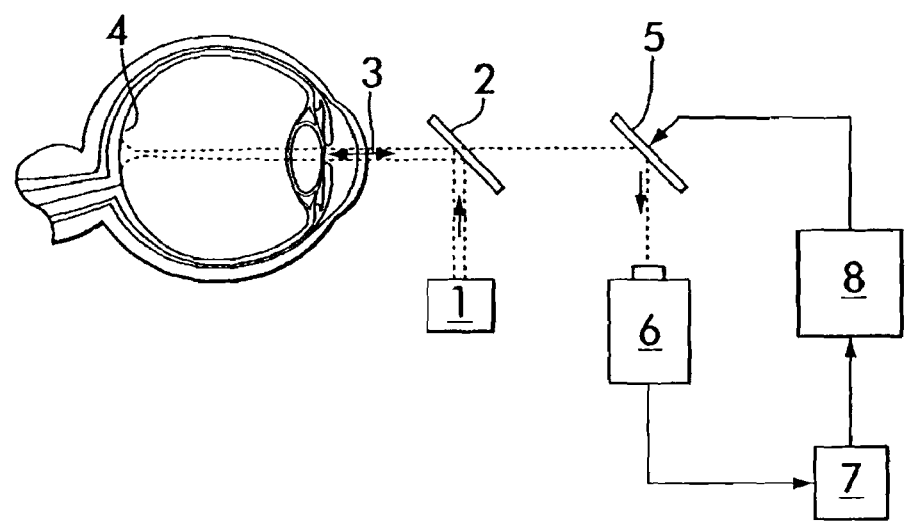

Referring now to FIGS. 1A,B, there are shown schematic representations of the aberration correcting system 10 of the present invention. In the aberration correcting system 10 a light beam from a white light source is redirected by a mirror in order to cause it to be applied to an eye. In accordance with the present invention, the white beam from the light source can be any kind of incoherent light. Furthermore, in a preferred embodiment of the invention, the energy source applied to the eye or other object being imaged can be a source of any kind of electromagnetic energy, and need not necessarily be light.

The light from the mirror 2 reaches the retina 4 of the eye and reflected light exits the eye to provide two light beams, one passing in each direction, as indicated by arrow 3. The exiting light beam then passes through an SLM 5. The light beam from the SLM 5 enters an image sensor 6. The sensor 6 can be a charge coupled capacitor device or any other device capable of sensing and digitizing the light beam from the SLM 5. In the embodiment of the invention wherein electromagnetic energy other than a light beam is used as an energy source, and therefore is caused to interact with the object, the energy resulting from the interaction, for example, energy reflecting off the object and/or energy transmitted through the object, can be used and processed in any manner appropriate for the frequencies of electromagnetic radiation used as an energy source. For example, the energy used and processed in the system of the invention can be sensed, redirected, measured, digitized, or processed in any other manner, by any sensors, measuring devices or energy processing devices known by those skilled in the art to be appropriate for the frequencies of electromagnetic energy used as an energy source. Furthermore, the signals representing the sensed, reflected, transmitted or otherwise processed electromagnetic energy interacting with the object can be any kind of signals known to those skilled in the art.

The imaging sensor 6 can include an imaging chip for performing the calculations required to determine an image quality metric. The image quality metric can thus be computed on the imaging chip directly or it can be calculated using a separate computational device/computer 7 that calculates the image quality metric of the retina image. It is the use of a digitized image in this manner that permits the use of an incoherent light rather than a coherent light for performing the operations of the aberration correction correcting system 10.

The computational device 7 sends a measurement signal representative of the image quality metric to a controller 8. The controller 8 implements a PSPGD algorithm by computing control voltages and applying the computed control voltages to the SLM 5. The PSPGD algorithm used by the controller 8 can be any conventional PSPGD algorithm known to those of ordinary skill in the art. In the preferred embodiment of the invention, the controller 8 continuously receives digital information about the quality of the image and continuously updates the control voltages applied to the SLM 5 until the quality of the retina image is optimized according to predetermined image quality optimization criteria.

Figure 2:
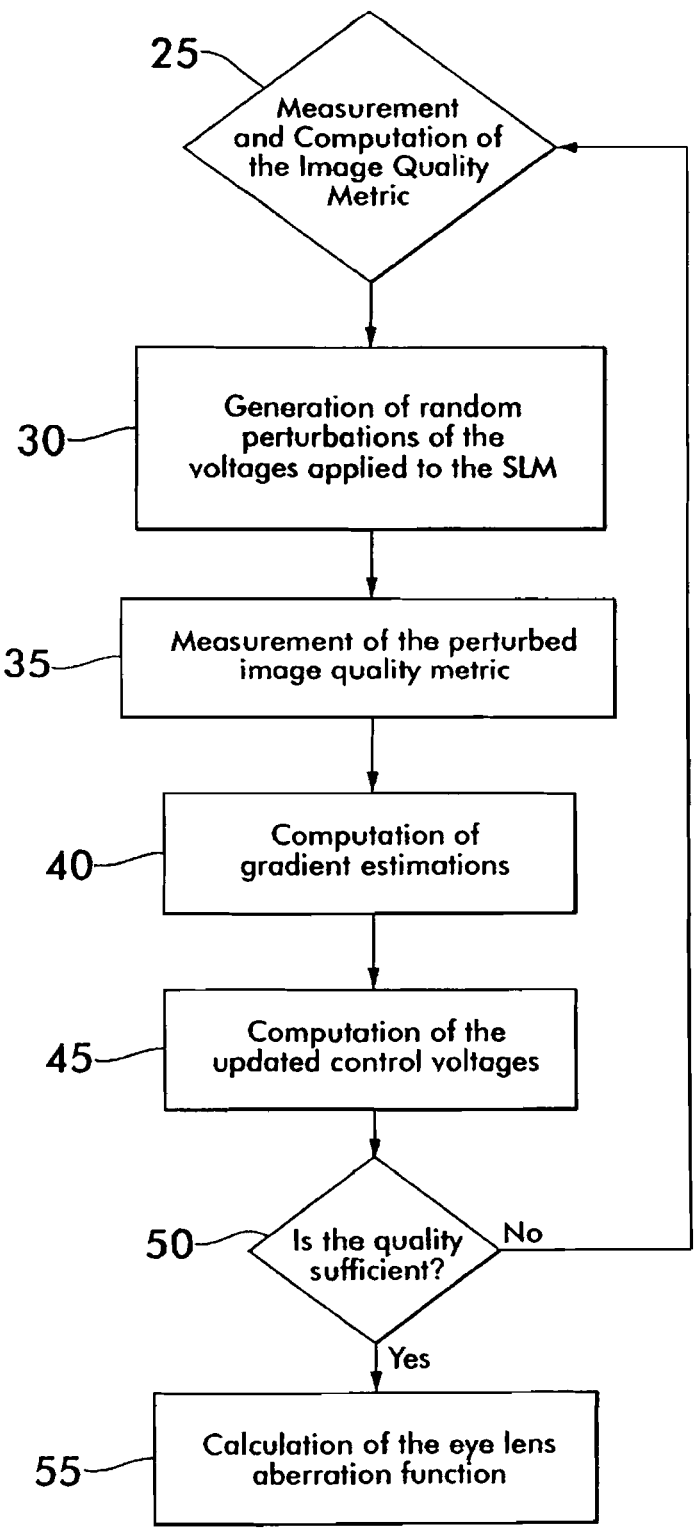
FIG. 2 shows a flow chart representation of control algorithm suitable for use in the system of FIG. 1 when practicing the method of the present invention.
Figure 3A:
FIGS. 3A,B show images of an artificial retina before and after correction of an aberration FIG. 4A,B show an eye and a biometric image of the iris of the eye.

Referring now to FIGS. 2 and 3A,B there are shown a flow chart representation of a portion of a PSPGD control algorithm 20 for use in cooperation with the aberration correcting system 10 in order to practice the present invention as well as representations of the corrected image, both before correction (3A) and after correction (3B). In order to simplify the drawing a single iterative step of the PSPGD control algorithm 20 is shown with a loop for repeating the single iterative step until the quality of the compensation is acceptable.

In step 25 of the PSPGD control algorithm 20 a measurement and calculation of the image quality metric is performed. This step includes the retinal image capture performed by the sensor 5 and the calculation of the image quality metric performed by the computational device 7 within the aberration correcting system 10. The image captured by the sensor 5 at the beginning of the operation of the PSPGD control algorithm 20 can be substantially as shown in FIG. 3A, as previously described. One can use any relevant metric entity as an image quality metric. For example, in one embodiment of the PSPGD control algorithm 20 the image quality metric can be a sharpness function. A sharpness function suitable for use in the present invention can be defined as $$J = \int |\nabla^2 I(x,y)| dx dy$$

where $I(x,y)$ is the intensity distribution in the image, and $\nabla^2$ is the Laplacian operator over the image. The Laplacian can be calculated by convolving the image with a Laplacian kernel. The convolving of the image can be performed by a special purpose VLSI microchip. Alternately, the convolving of the image can be performed using a computer that receives an image from a digital camera as described in more detail below. In another embodiment different digital high-pass filters can be used rather than the Laplacian operator.

Additionally, a frequency distribution function can be used rather than a sharpness function when determining the image quality metric. The use of a frequency distribution function allows the system to distinguish tissues of different colors. This is useful where different kinds of tissue, for example, different tumors, have different colors. Locating tumors in this manner also permits the invention to provide tumor location information, such as a grid location on a grid having a pre-determined reference in order to assist in diagnosis and surgery. It also permits the invention to provide tumor size and type information. Additionally, the use of a frequency distribution function permits a surgeon to determine which light frequencies are best for performing diagnosis and surgery.

The image quality metric J can also be calculated either optically or digitally using the expression introduced in:

$$J = \int |F\{\exp[i\gamma I(x,y)]\}|^4 dxdy$$

Where F is the Fourier transform operator and γ is a parameter that is dependent upon the dynamic range of the used image.

In step 30 of the PSPGD control algorithm 20 random perturbations in the voltages applied to the SLM 5 electrodes are generated. The SLM 5 can be a liquid crystal membrane for modifying the light beam according to the electrical signals from controller 8 in a manner well understood by those skilled in the art.

In order to generate the perturbations for application to the electrodes for the SLM 5 random numbers with any statistical properties can be used as perturbations. For example, uncorrelated random coin flip perturbations having identical amplitudes |$u_j$ and the Bernoulli probability distribution:

$$du_j = \pm p, Pr(du_j = +p) = 0.5$$

for all j=1, ..., N (N=the number of control channels) and iteration numbers can be used. Note that Non-Bernoulli perturbations are also allowed in the PSPGD control algorithm 20.

In step 35 of the PSPGD control algorithm 20 a measurement of the perturbed image quality metric and a computation of the image quality perturbation $\delta J^{(m)}$ are performed. Following the determination of the perturbed image quality metric, the gradient estimations $$J'^{(m)}_j = \delta J^{(m)} \pi_j^{(m)}$$

are computed as shown in step 40.

The updated control voltages are then determined as shown in step 45. Therefore, a calculation of:

$$u_j^{(m+1)} = u_j^{(m)} - \gamma \delta J^{(m)} \pi_j^{(m)}$$

is performed.

To further improve the accuracy of gradient estimation in the PSPGD control algorithm 20 a two-sided perturbation can be used. In a two-sided perturbation two measurements of the cost function perturbations $J^+$ and $J^-$ are taken. The two measurements correspond to sequentially applied differential perturbations $+u_j/2$ and $-u_j/2$.

It follows that:

$$dJ = dJ^+ - dJ^- \text{ and}$$

$$J'_j = \delta J \delta u_j$$

which can produce a more accurate gradient estimate.

Figure 3B:
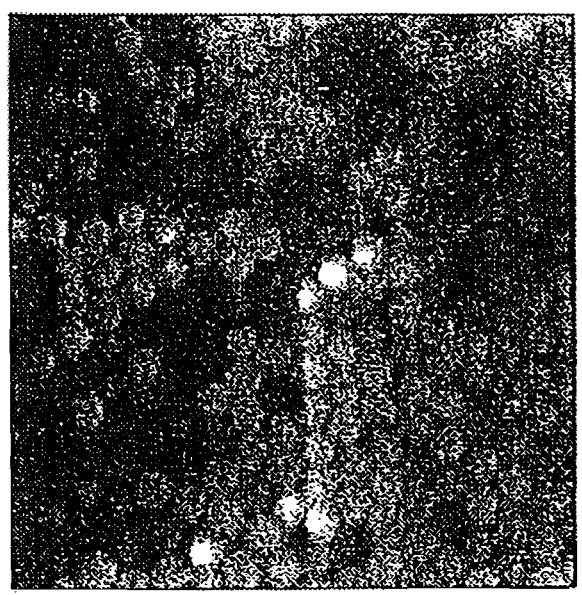

The process steps 25-45 of the PSPGD control algorithm 20 are repeated interactively until the image quality metric has reached an acceptable level as determined in step 50. The choice of an acceptable level of the image quality metric is a conventional one well known to those skilled in the art. As shown in step 55 the aberration is then corrected and an image of the retina can be taken. The image resulting from the operation of the PSPGD algorithm 20 can be as shown in FIG. 3B.

The eye aberration function (x,y) can be calculated from known voltages applied to wavefront correction {$u_j$} at the end of the iterative optimization process and known response functions of {$S_j(x,y)$} wavefront correction.

$$j(x, y) = \sum_{j=1}^{N} u_j S_j(x, y).$$

Referring now to FIGS. 4A,B, there is shown an eye 80 having an iris 84 with a pupil 88 therein and an iris biometric image 90. The iris biometric image 90 is a biometric image of the iris 84, which can be obtained using an iris scanning system, such as the aberration correcting system 10. In an alternate embodiment of the invention, the iris biometric image 90 can be obtained by any other system (not shown) capable of scanning and digitizing an iris and providing an image that is characteristic of the iris, such as a bar code type output as shown in FIG. 4B. Furthermore, it will be understood that every human eye has an unique iris biometric image when it is scanned and digitized in this manner. Thus, an iris biometric image can be used as a unique identifier of an individual in the manner that fingerprints are used or even to distinguish between the left and right eyes of an individual.

When the predetermined image quality is obtained, a plurality of locations 92 within the iris 84 can be defined. In one preferred embodiment of the invention, four locations 92 can be selected. The four locations 92 can be disposed on the corners of a rectangle which is concentric with the iris 84. The locations 92 can thus be easily used to find the center of the iris 84. The four locations 92 are represented on the iris biometric image 90 in accordance with the mathematical relationships previously described. Thus, the xy coordinates of the locations 92 may be mapped into corresponding xy coordinates within the iris biometric image 90 if a spatial transform such as the sharpness function is used, while they may be convolved over areas of the iris biometric image 90 if a frequency or other transform is used.

Various features already occurring in the eye 80 also have corresponding representations within the iris biometric image 90. The location and study of such features can be used to diagnose pathologies, for example, to diagnose tumors and to determine the position of the eye iris 84. As a further example, a feature can be studied several times over a period of time to determine how its parameters are is changing.

Figure 5:
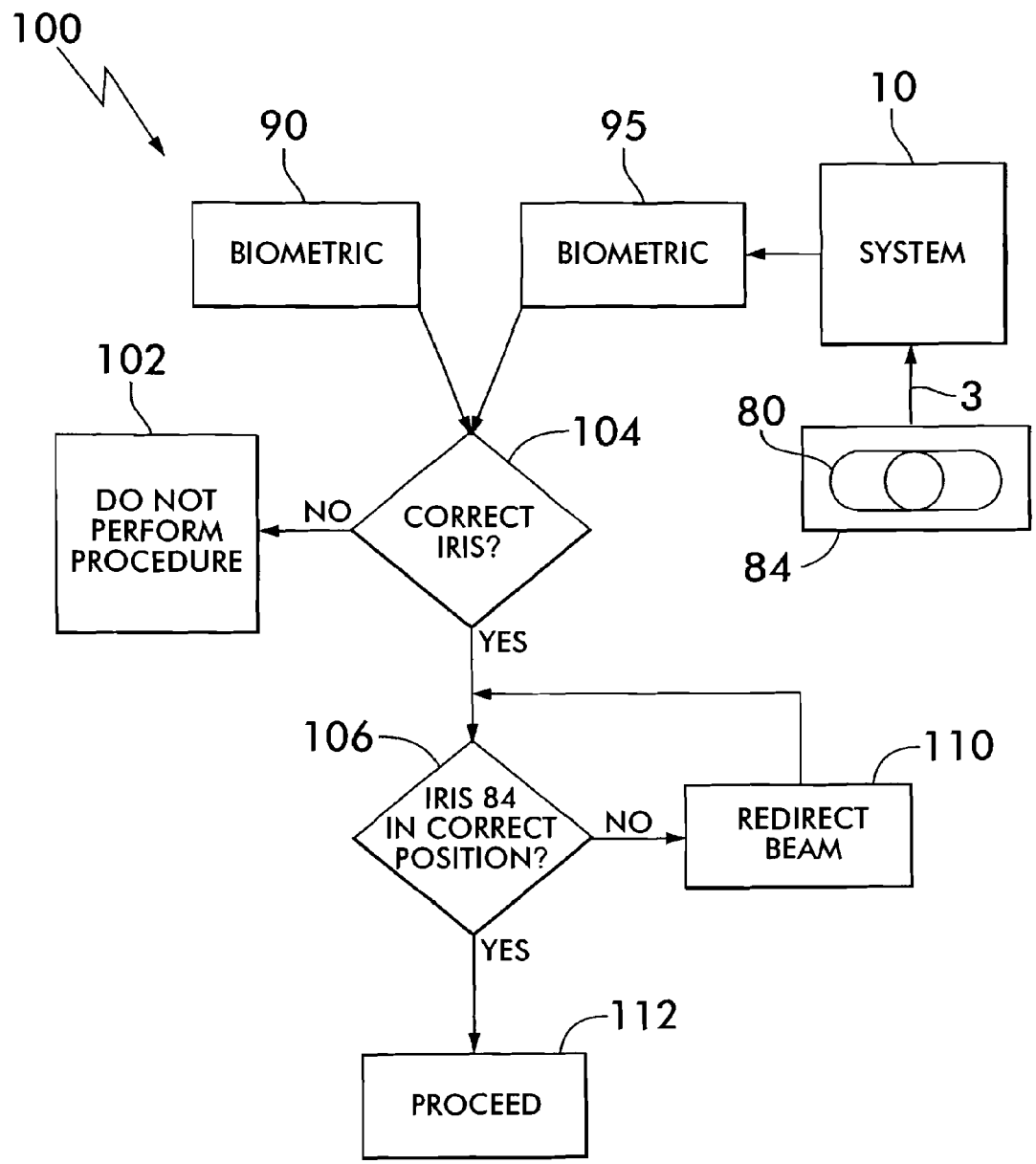
FIG. 5 shows a block diagram representation of an iris biometric image comparison system which can be used with the aberration correcting system of FIG. 1.

Referring now to FIG. 5, there is shown the iris biometric image comparison system 100. The iris biometric image comparison system 100 receives the previously determined iris biometric image 90 as one of its inputs. Additionally, a new iris biometric image 95 is produced, for example, before or during the performance of a procedure on the eye 80. The new iris biometric image 95 is received by the image comparison system 100 as a second input. The new iris biometric image 95 can be provided by the aberration correction system 10| The light beam used to obtain the iris biometric image 95 can be the same light beam being used for other purposes during the procedure.

When using the aberration correcting system 10, the image can be optimized by executing additional iterations of the PSPGD control algorithm 20. The algorithm can be iterated until a predetermined image quality is obtained and computing the image quality metric within the computer 7 as previously described. In addition to performing more iterations of the PSPGD control algorithm 20, increased image sensitivity quality can be obtained by increasing the number of pixels in the digitized image or increase image sensitivity can be obtained by increasing the number of measuring points in the iris 84.

When performing the method of the image comparison system 100 the iris biometric image 90 can be assumed by the image comparison system 100 to be the correct iris biometric image of the iris 84 upon which the procedure is to be performed. Furthermore, it can be assumed that the iris biometric image 90 applied to the image comparison system 100 was obtained when the position and orientation of the eye 80 were correct.

The iris biometric images 90, 95 are compared by the image comparison system 100 at decision 104. A determination is made as to whether the iris biometric image 95 is an image of the same iris 84 that was imaged to produce the enrolled iris biometric image 90. Any of the well known correlation techniques can be used for the comparison. Substantially similar correlation techniques can be used for the comparison if the locations 92 are used or if other markings within the iris 84 are used. The sensitivity of the comparison can be adjusted by those skilled in the art.

If the determination of decision 104 is negative, then the procedure being performed on the eye 80 is not continued as shown in block 102. If the determination of decision 104 is positive, then a determination can be made in decision 106 whether the iris 84 is positioned in the xy directions correctly and oriented or rotated correctly at the time that the iris biometric image 95 was produced. The determination of decision 106 can be used for a number of purposed. For example, it could be used to direct a beam of light to a predetermined location within the eye 80. Thus, if the determination of decision 106 is negative, the beam can be redirected as shown in block 110. The position of the iris 84 can be checked again in decision 106. When the position of the iris 84 is correct, the procedure can begin, as shown in block 112.

The determination of decision 106 can be made in accordance with the representations of locations 92 within the iris 84 selected when iris biometric image 90 was obtained. If corresponding locations are found in the iris biometric image 95 in the same positions, the determination of decision 106 is positive. Alternately, the determination of decision 106 can be made in accordance with predetermined features or markings within the iris 84 other than the locations 92. The method of the image comparison system 100 can be used to determine whether the iris 84 is rotated or translated in the direction of either of the axes orthogonal to the arrow 3 shown in FIGS. 1A,B.

Figure 6:
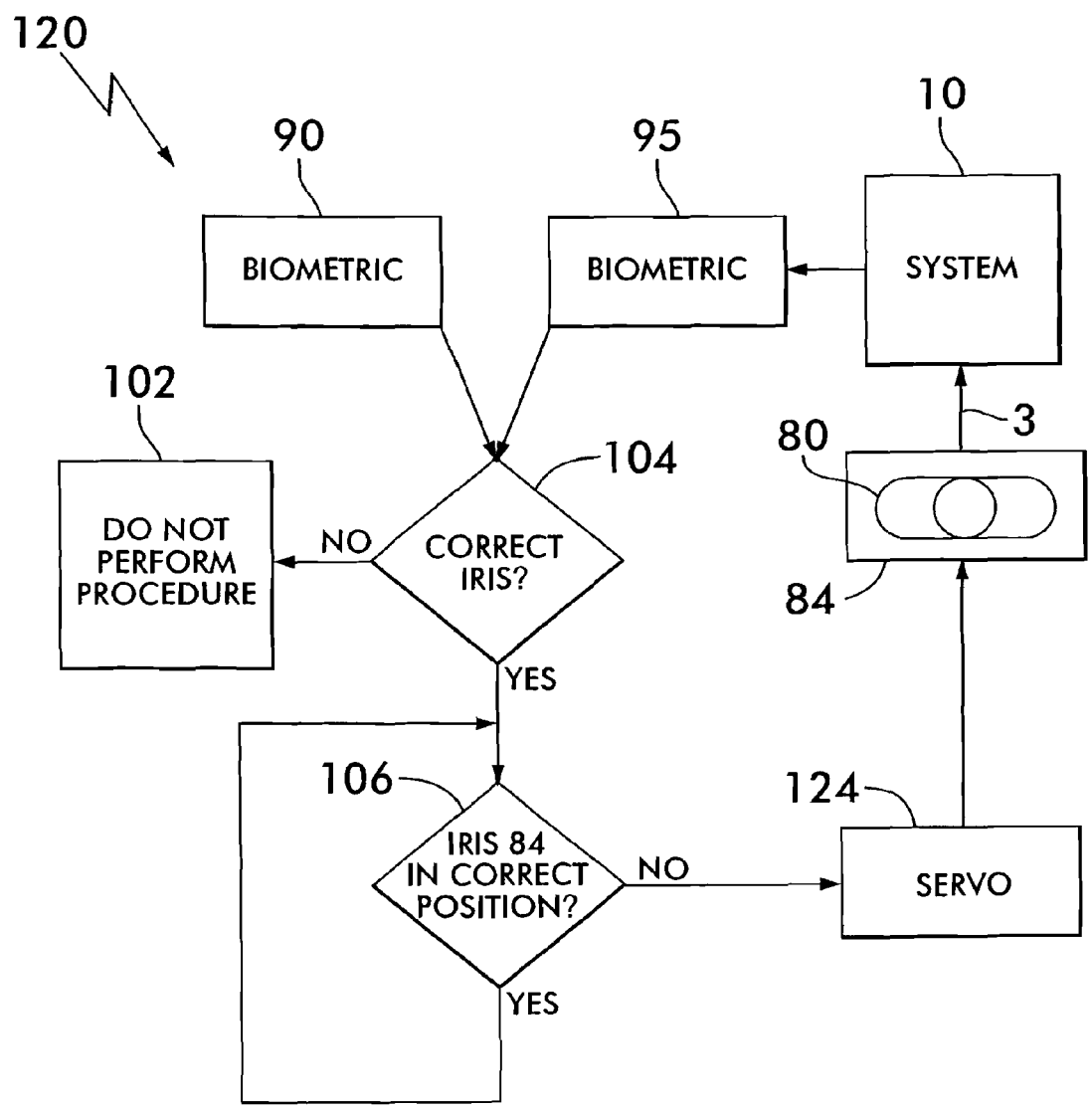
FIG. 6 shows a block diagram representation of an iris positioning system which can be used in cooperation with the aberration correcting system of FIG. 1.

Referring now to FIG. 6, there is shown the iris positioning system 120. The iris positioning system 120 is adapted to precisely position the iris 84 while performing a procedure on the eye 80. The iris positioning system 120 differs from the iris biometric image comparison system 100 primarily in the fact that the iris positioning system 120 is provided with a servo 124. The servo 124 is effective in modifying the relative positions of the iris 84 and the camera 6 of the aberration correcting system 10 which can be coupled to equipment (not shown) used to perform the procedure in the eye.

In the iris positioning system 120 a determination is made in decision 104 whether the iris biometric images 90, 95 were made on the same eye as previously described with respect to image comparison system 100. The procedure is continued only if a positive determination is made. A determination is then made in decision 106 whether the iris 84 is in the correct position. The determination of decision 106 can be made by comparing the iris biometric images 90, 95 in accordance with the locations 92 or any other markings within the iris 84 as previously described. The determination made can be, for example, whether the iris 84 is rotated or translated in the x or y direction at the time that the iris biometric image 95 is obtained.

When a determination is made that the iris 84 is in an incorrect position, a correction signal representative of the error is calculated. The error correction signal is applied to the servo 124. The servo 124 is adapted to receive the error correction signal resulting from the determinations of decision 106 and to adjust the relative positions of the iris 84 and the equipment performing the procedure in accordance with the signal in a manner well understood by those skilled in the art. Servos 124 capable of applying both rotational and multi-axis translational corrections are both provided in the preferred embodiment of the invention. Either the object such as the iris 84 or the equipment can be moved in response to the determination of decision 106.

The method of the iris positioning system 120 can be repeatedly performed, or constantly performed, during the performance of a procedure on the eye 80 to re-capture, re-evaluate or refine the process the eye 80. Thus, the relative positions of the iris 84 and the procedure equipment can be kept correct at all times.

Figure 7:
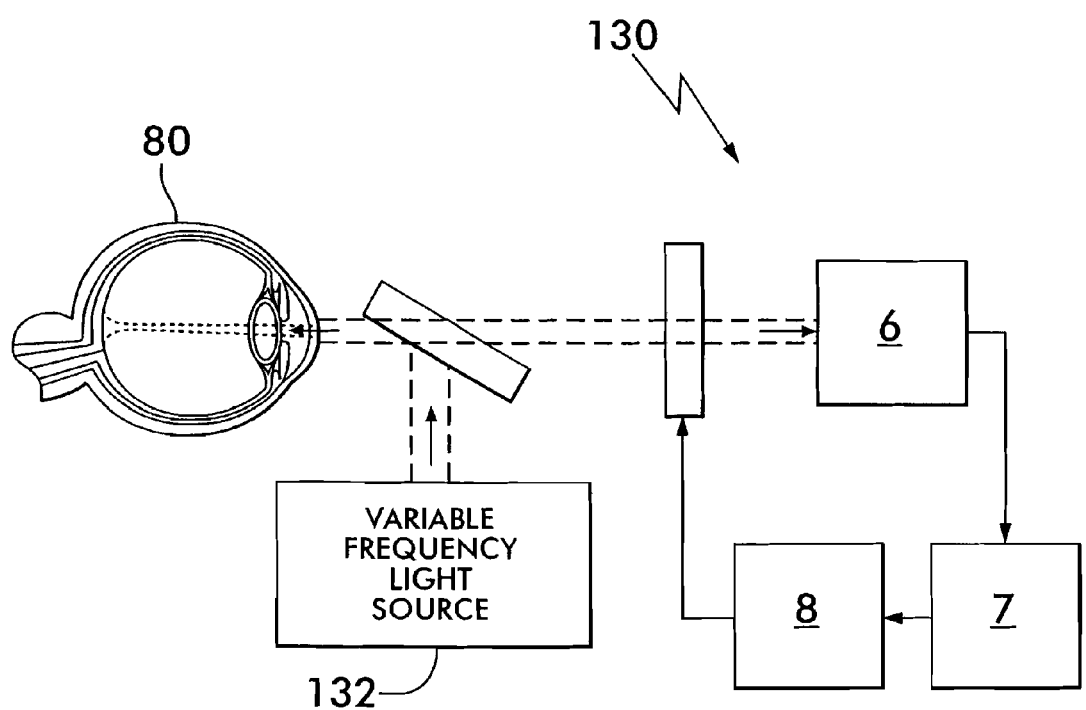
FIG. 7 shows an illumination frequency optimization system which can be used in cooperation with the aberration correcting system of FIG. 1.

Referring now to FIG. 7, there is shown the illumination frequency optimization system 130. The illumination frequency optimization system 130 is an alternate embodiment of the aberration correcting system 10. Within the frequency optimization system 130 a variable frequency light source 132 rather than a single frequency light source applies a light beam to the eye 80. The variable frequency light source 132 can be a tunable laser, a diode, filters in front of a light source, a diffraction grating or any other source of a plurality of frequencies of light. An image quality metric can be obtained and optimized in the manner previously described with respect to system 10.

Using the variable frequency light source 132, it is possible to conveniently adjust the frequency of the light beam used to illuminate the eye 80 or object 80 at a plurality of differing frequencies and to obtain a plurality of corresponding image quality metrics. In order to do this, the frequency of the light applied to the eye 80 by the variable frequency light source 132 can be repeatedly adjusted and a new image quality metric can be obtained at each frequency. Each image quality metric obtained in this manner can be optimized to a predetermined level. The levels of optimization can be equal or they can differ. While the optimizations should be done using the frequency distribution, it is possible to return to images optimized using the frequency distribution and sharpen using the sharpness function.

It is well understood that differing types of tissue can be visualized best with differing frequencies of light. For example, tumors, lesions, blood and various tissues as well as tissues of varying pathologies can be optimally visualized at different frequencies since their absorption and reflection properties vary. Thus, by adjusting the frequency applied to the eye 80 by the variable frequency light source 132 and viewing the results, the best light for visualizing selected features can be determined. Furthermore, using this method there can be several optimized images for one eye. For example, there can be different optimized images, for a tumor, for a lesion and for blood. The determination of the best frequency for each image can be a subjective judgment made by a skilled practitioner.

A skilled practitioner can use the illumination frequency optimization system 130 to emphasize and de-emphasize selected features within images of the eye 80. For example, when obtaining an iris biometric image 95, the iris 84 may be clouded due to inflammation of the eye 80 or the presence of blood in the eye 80. It is possible to effectively remove the effects of the inflammation blood with the assistance of the frequency optimization system 130 by varying the frequency of the light provided by the light source 132 until the optimum frequency is found for de-emphasizing the inflammation or blood and permitting the obscured features to be seen. In general, it is often possible to visualize features when another feature is superimposed on them by removing the superimposed feature using system 130.

In order to remove the effects of the inflammation or blood, a plurality of images of the eye 80 can be provided and the frequency at which the blood or inflammation is least apparent can be determined. Removing these features from the iris biometric image 95 can facilitate its comparison with the iris biometric image 90. Furthermore, when the biometric image 95 is obtained from the iris 110 of a person wearing sunglasses, it is possible to remove the effects of the sunglasses in the same manner and identify an eye 80 behind the sunglasses. This feature is useful when identifying people outside of laboratory conditions.

Figure 8:
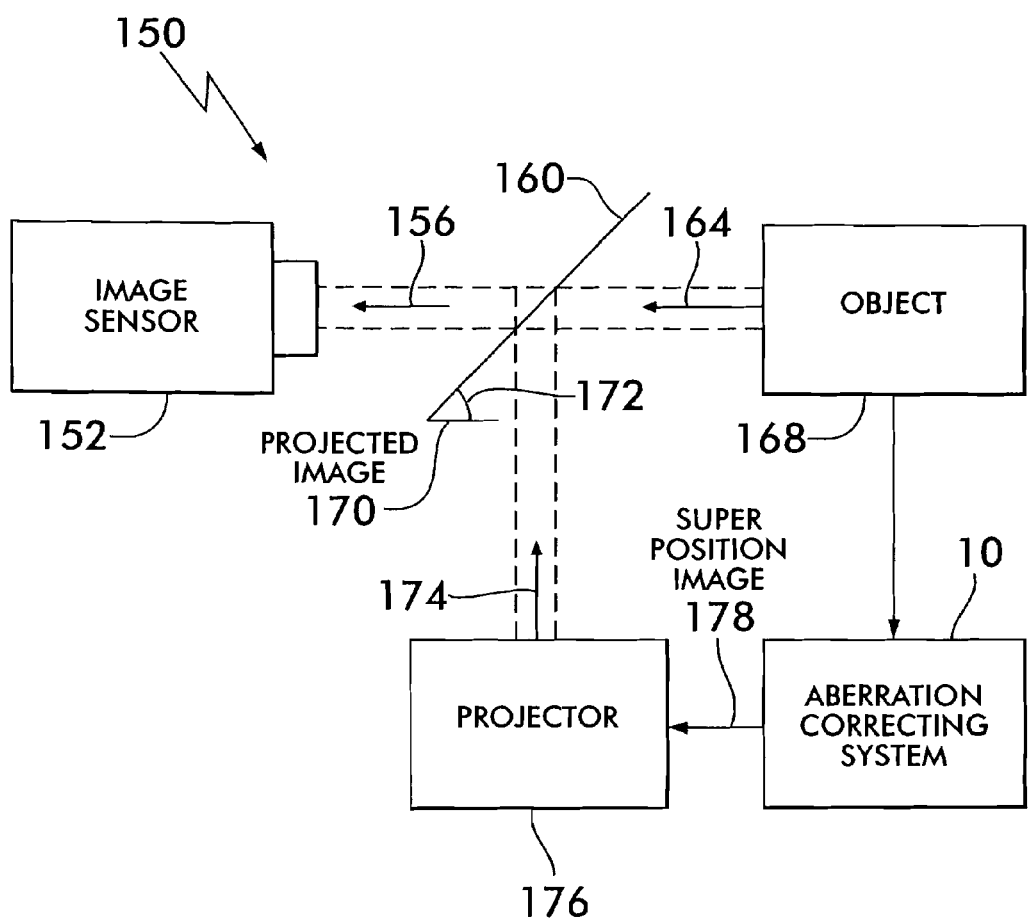
FIG. 8 shows an image superpositioning system which can be used with the aberration correcting system of FIG. 1.

Referring now to FIG. 8, there is shown the image superposition system 150. In many cases it is desirable to perform a procedure on an eye 80 when selected features of the eye 80 are obscured by other features, where different features are visualized best at different frequencies, or where the criteria for emphasizing and de-emphasizing features can change during a procedure. Image superposition 100 can be used to obtain improved feature visualization under these and other circumstances.

For example, white light is often preferred for illuminating an iris 84 because in many cases white light shows the most features. However, if white light is used to illuminate an iris 84 when the iris 84 is clouded with blood, the blood can block the white light. This can make it difficult, or even impossible, to visualize the features that are obscured by the blood. One solution to this problem is to use red light to illuminate the iris 84 and visualizes the features obscured by the blood.

However, the red light could fail to optimally visualize the features which are normally visualized best using, for example, white light. The image superposition system 150 can solve this problem by superimposing two images such as the direct image 166 and the projected image 170, where the images 166, 170 are obtained using light sources of differing frequencies. The optimum frequencies for obtaining each of the images 166, 170 can be determined using the illumination frequency optimization system 130.

For example, an object 168 to be visualized can be illuminated with incoherent white light to provide the direct image 166. Illumination of the object 168 by white light to produce the direct image 166 can be provided using any of the known methods for providing such illumination of objects to provide digital images. The direct image 166 can be sensed and digitized using an image sensor 152 which senses light traveling from the object 168 in the direction indicated by the arrows 156, 164.

The image sensor 152 senses the direct image 166 of the object 168 by way of a superposition screen 160. The superposition screen 160 can be formed of any material capable of transmitting a portion to the light applied to it from the object 168 to the image sensor 152, and reflecting a portion of the same light. For example, the superposition screen 168 can be formed of glass or plastic. A viewer, a TV screen or a gradient filter can also serve as the superposition screen 160. The screen 160 can also be a gradient filter. In a preferred embodiment of the invention, the angle 172 of the superposition screen 160 can be adjusted to control the amount of light it transmits and the amount it reflects.

The projected image 170 of the object 168 can be obtained using, for example, the aberration correcting system 10 as previously described. Illumination with red light or any other frequency of light can be used within the aberration correcting system 10 to obtain the superposition image 178. The superposition image 178 is applied to an image projector 176 by the aberration correcting system 10. The image projector 176 transmits the projected image 170 in accordance with the superposition image 178 in the direction indicated by the arrow 174 and applies it to the superposition screen 160.

A portion of the projected image 170 applied to the superposition screen 160 by the projector 176 is reflected off of the superposition screen 160 and applied to the image sensor 152 in the direction indicated by the arrow 156. The amount of the projected image 170 reflected to the image sensor 152 can be adjusted by adjusting the angle 172 of the superposition screen 160. The image projector 176 is disposed in a location adapted to apply the projected image 170 to the superposition screen 160 in the same region of the superposition screen 160 where the direct image 166 is applied. When the images 166, 170 are applied to the superposition screen 160 in this manner, they are superimposed and the image sensed by the image sensor 152 is thus the superposition or composite of the images 166, 170.

Adjustment of the angle 172 results in emphasizing and de-emphasizing the images 166, 170 relative to each other. This is useful, for example, where different features visualized selectively at differing frequencies must be brought in and out of visualization in the composite image for different purposes. Another time where this is useful is when the intensity of one of the images 166, 170 is too high relative to the other and must be adjusted down or too low and must be adjusted up.

In various alternate embodiments of the image superposition system 150, either or both of the images 166,170 can be optimized using the PSPGD algorithm 20 within the aberration correction system 10. Furthermore, the images 166, 170 can be optimized to differing degrees by the PSPGD algorithm 20 and with differing optimization criteria in order to emphasis one over the other or to selectively visualize selected features within the images 166,170 and thus, within the composite image sensed by image sensor 152. This permits selected features of the eye 80 to be brought into view and brought out of view as convenient at different times during a diagnosis or a procedure.

Thus, the illumination used to obtain the images 166, 170 superimposed by the image superposition system 150 does not need to be red and white light. The illumination used can be light of any differing frequencies. The frequencies selected for obtaining the images 166,170 can be selected in accordance with the sharpness function on the frequency distribution as previously described.

The images superimposed by the image superposition system 150 do not need to be obtained by way of a camera, such as the camera 6 of the aberration correction system 10. A microscope, an endoscope, or any other type of device having an image sensor capable of capturing transmission, absorption or reflection properties of an object or tissue in a normal state or enhancement by such materials as markers and chromophores and thereby providing an optical/digital signal that can be applied to the computer 7 for optimization using the PSPGD algorithm 20 can be used. Thus, for example, an image obtained from an endoscope or a microscope can be superimposed upon an image obtained from an camera using the method of the present invention. Images from endoscopes, microscopes and other devices can be digitized, and superimposed and synthesized with each other. It will be understood that images obtained from such devices and optimized using the PSPGD algorithm 20 can be used in any other way that images obtained from the PSPGD algorithm 20 using camera 6 are used.

The description herein will so fully illustrate my invention that others may, by applying current or future knowledge, adopt the same for use under various conditions of service. For example, the invention may be used for opthalmological procedures such as photocoagulation, optical biopsies such as measuring tumors anywhere in the eye, providing therapy, performing surgery, diagnosis or measurements. Additionally, it can be used for performing procedures on eyes outside of laboratory or medical environments. Furthermore, the method of the present invention can be applied to any other objects capable of being imaged in addition to eyes and images of an object provided. In accordance with the method of the invention can be used when performing such procedures on other objects.

While the invention has been described in detail and with reference to specific examples thereof, it will be apparent to one skilled in the art that various changes and modifications can be made therein without departing from the spirit and scope thereof.

The invention claimed is:

1. A device comprising:
   (a) an electromagnetic energy source; and
   (b) a sensor for capturing reflected and/or transmitted energy from an object exposed to said energy source, wherein said reflected and/or transmitted energy is received through a:
      (i) spatial energy modulator in communication with
      (ii) a controller comprising a parallel stochastic perturbation gradient descent or a simultaneous perturbation stochastic approximation optimization algorithm.

2. The device of claim 1, wherein said spatial energy modulator is a pixelized liquid crystal device, a micromechanical mirror array, a piston mirror, a tip-tilt mirror or a deformable mirror.

3. The device of claim 1, wherein said sensor is a CCD camera, a CMOS camera or a very large scale integration imaging device.

4. The device of claim 1, wherein said controller comprises a parallel controller.

5. The device of claim 1, further comprising an integral device for executing said algorithm computations.

6. The device of claim 1, wherein the energy source is a variable frequency source.

* * * * *